United States Patent [19]

Kouwenhoven et al.

[11] Patent Number: 5,324,872
[45] Date of Patent: Jun. 28, 1994

[54] PROCESS FOR THE PREPARATION OF NITROBENZENE

[75] Inventors: Herman W. Kouwenhoven, Herrliberg; Leopoldo Bertea; Roel Prins, both of Zürich, all of Switzerland

[73] Assignee: CU Chemie Uetikon AG, Uetikon, Switzerland

[21] Appl. No.: 986,024

[22] Filed: Dec. 4, 1992

[30] Foreign Application Priority Data

Dec. 4, 1991 [CH] Switzerland .............. 03554/91

[51] Int. Cl.$^5$ ............................ C07C 205/06
[52] U.S. Cl. .................... 618/927; 568/932
[58] Field of Search .................. 568/927, 932

[56] References Cited

U.S. PATENT DOCUMENTS

| Re. 33,549 | 5/1991 | Weigert | 564/409 |
|---|---|---|---|
| 3,966,830 | 6/1976 | Shimada et al. | 568/937 |
| 4,107,220 | 8/1978 | Owsley et al. | 568/937 |
| 4,371,721 | 2/1983 | Wu | 568/946 X |
| 4,415,744 | 11/1983 | Schumacher et al. | 560/20 |
| 4,418,230 | 11/1983 | Bakke et al. | 568/940 |
| 4,754,083 | 6/1988 | Reith et al. | 568/932 |
| 4,891,448 | 1/1990 | Garces et al. | 568/628 |
| 5,194,244 | 3/1993 | Brownscombe et al. | 423/700 |

FOREIGN PATENT DOCUMENTS

| 0078247 | 5/1983 | European Pat. Off. |
| 0092372 | 10/1983 | European Pat. Off. |
| 0317907 | 5/1989 | European Pat. Off. |
| 0343048 | 11/1989 | European Pat. Off. |

Primary Examiner—Robert L. Stoll
Assistant Examiner—Valerie Fee
Attorney, Agent, or Firm—Fisher & Associates

[57] ABSTRACT

The invention concerns a gasphase process for the preparation of nitrobenzene from benzene and nitric acid, wherein catalysts are applied based on the zeolite mordenite.

5 Claims, No Drawings

PROCESS FOR THE PREPARATION OF NITROBENZENE

This invention relates to the zeolite mordenite and its application as a catalyst in the gasphase nitration of benzene to nitrobenzene using nitric acid as nitrating agent. Processes for the gasphase nitration of aromatics in which $NO_2$ or other nitrogen oxides are applied as nitrating agents have been mentioned in the relevant literature. A review presented in U.S. Pat. No. 4,754,083 shows that a large variety of materials has been claimed as catalysts in the gasphase nitration of aromatics using nitrogen oxides as nitrating agents. In the review in U.S. Pat. No. 4,754,083 zeolites and other crystalline or amorphous aluminosilicates are frequently mentioned as particular effective catalysts.

In U.S. Pat. No. 4,754,083 molecular sieves, montmorillonite and pillared bentonite are claimed in general as catalysts in the gasphase nitration of substituted aromatics containing a meta directing group such as $NO_2$. Experiments are described concerning the gasphase nitration of nitrobenzene using catalysts based on a large number of different zeolites, such as Zeolon 900H; H-Y; H-Beta; H-ZSM-5 and H-erionite. In these experiments both a fixed bed and a fluidized bed reactor were used, and in the results the conversion obtained after one to two hours reaction time is reported. The data are accordingly not sufficient to assess the stability of the catalysts in experiments of longer duration. The preferred catalysts, which were based on zeolite Na-X and H-fenierite, had a low conversion activity (<25%) and a high selectivity for the formation of p-dinitrobenzene. A gasphase process for the manufacture of nitrobenzene using nitric acid as nitrating agent is proposed in EPA 343.048, acidic layered silicates and/or acidic oxidic materials are applied as catalysts. The latter consist of oxides of group WA of the periodic system in combination with one or more of the following oxides: tungsten trioxide, molybdenum trioxide or zinc oxide. The performance of the catalysts described in EPA 343.048 is said to be very good and moreover stability, activity and selectivity of the claimed materials is supposedly better than those of other materials which were described in earlier publications and/or patents.

The application of catalysts based on H-mordenite in the gasphase nitration of aromatics using resp. $NO_2$, $N_2O_3$ or $N_2O_4$ and preferentially $NO_2$, as nitrating agent is described in a patent series comprising a.o. EP 53.053; EP 78.247; EP 92.372 and U.S. Pat. No. 4,107,220. The mordenite based catalysts as described in these patents are commercial products, which were available from the Norton Cy under the Tradename "Zeolon-x00H, e.g. Zeolon 900H or Zeolon 200H. In the descriptions given in the patents mentioned earlier in this paragraph the materials are preferentially pretreated at reaction conditions with the nitrating agent and further no additional pretreatment is considered as beneficial for catalyst performance.

In DEOS 28.26.433 and U.S. Pat. No. 4,418,230, the gasphase nitration of toluene with nitric acid is described using Zeolon 200H as a catalyst. Also in these patents no further pretreatment leading to an improved catalyst performance is mentioned, experiments were carried out at 473 K, atmospheric pressure and a toluene/nitric acid molar ratio of about 1.4. No data were presented relating to the stability of the performance of the mordenite based catalyst. In fact most of the experimental results relate to the application of a catalyst based on montmorillonite, which had a much better performance than the mordenite based catalyst.

Mordenite is a molecular sieve zeolite, which occurs in the earth's crust as a mineral and which may also be synthetically prepared. Mordenite has the general composition $Na_8[Al_8Si_{40}O_{96}].24H_2O$, the crystallographic structure of mordenite is described in the "Atlas of Zeolitic Structure Types" by W. M. Meier and D. H. Olson, 2nd edition, published by Butterworth in 1987 on behalf of the Structure Commission of the Intimation Zeolite Association. The mordenite lattice has, due to the substitution of four valent silicon atoms by trivalent aluminum atoms, a negative electric charge, which is compensated by the exchangeable sodium atoms. In many an application of zeolites in catalysis acidic zeolites are used, which are usually described as H-zeolites. H-mordenite is usually prepared by ion-exchange processes, either direct with acids or indirect via ion-exchange with an ammonium salt followed by calcination for removal of ammonium. The method applied for the preparation of H-mordenite often has a deciding effect on its performance as a catalyst in an acid-catalyzed reaction. This effect of catalyst preparation on catalyst performance is for instance clearly shown in U.S. Pat. No. 4,891,448 and in EPA 317.907 for the application of H-mordenite catalysts in the alkylation of biaromatics and in DEOS 1.816.448 for the application of H-mordenite catalysts for the isomerization of light paraffins. From these and many other publications it is clear that no single method exists for the preparation of the optimal H-mordenite catalyst for application in different reactions and that rather for each application of H-mordenite catalysts the optimal preparation procedure is to be developed in a systematic research effort.

The catalytic gasphase nitration of aromatics according to the present invention is carried out using catalysts based on mordenite. The catalysts are prepared from Na-mordenite by the combined application of ion-exchange and calcination. As a result of these treatments firstly Na ions are completely or partially removed and replaced by protons and secondly Al atoms are removed from their crystallographic positions in the mordenite lattice and presumably replaced by Si atoms. The sites of the Al and Si atoms in the mordenite lattice are commonly described as T-sites, which is an abbreviation for lattice positions having a tetrahedral oxygen coordination. The Al atoms which are removed from their lattice positions form oxo-aluminum species as a separate phase intermingled with the mordenite crystals. The oxo-aluminum species so formed can usually be removed by extraction with an acid. According to the present invention the catalytic gasphase nitration of aromatics is carried out in a continuous reactor, at a temperature between 373 and 623 K, preferably at a temperature between 423 and 523 K, using as a nitrating agent nitric acid, having a $HNO_3$ content higher than 15% wt, more preferentially having a $HNO_3$ content higher than 50% wt, and as catalysts materials based on the zeolite mordenite are applied. Surprisingly it was found that in the gasphase nitration of aromatics the performance of H-mordenite based catalysts is strongly affected by a calcination at a temperature higher than 823 K and that the performance of a thus calcined material is appreciably improved by a subsequent extraction with an acid.

The invention is illustrated by examples in the following paragraphs. The catalyst preparation is illustrated in examples 1 through 5.; the testing of comparative catalysts is described in examples 6 through 9 and the testing of the catalysts prepared according to the present invention and that of Norton 900H is described in the examples 10 through 20.

PREPARATION OF THE CATALYSTS

Example 1

Catalysts were prepared starting from commercial mordenite, type PM1-Na, available from CU Chemie Uetikon. Analytical data may be found in Table 1. The material was subjected to the following activation procedure: 500 g of PM1-Na was slurried in 5000 ml of a 1 molar solution of HCl in water and while sniffing the slurry was heated for one hour at 373 K. The solids were filtered off and subsequently washed with 5000 ml of demineralized water. The filtercake was dried in air during one hour at 373 K, the dried material is sample A. 50 g of sample A was slurried in 500 ml of a 1 molar solution of $NH_4NO_3$ in water and the stirred slurry was heated during one hour at 373 K. The solids were subsequently filtered off and washed with 500 ml of demineralized water. The product was again slurried in 500 ml of a 1 molar $NH_4NO_3$ solution in water and the stirred slurry was heated at 373 K for one hour. The solids were subsequently filtered off and washed with 500 ml demineralized water. A first part of the filtercake was dried in air during 16 hours at 393 K and subsequently calcined in an open crucible at 773 K during 3 hours, the product is sample B; a second part of the filtercake was calcined for 5 hours at 823 K in a covered crucible, the product is sample C; a third part of the filtercake was calcined during 5 hours at 973 K, the product is sample D. Analytical data on the samples B, C and D are collected in Table 1.

Example 2

200 g of sample A was slurried in 1000 ml of a 1 molar aqueous HCl solution and heated during one hour at 373 K while stirring. The solids were filtered off and washed three times with 500 ml demineralized water. The filtercake was reslurried in 1000 ml of I molar HCl and the treatment at 373 K was repeated once. The solids were filtered off and washed three times with 500 ml demineralized water. The filtercake was dried during 16 hours in air at 393 K, the dried product is sample E, analytical data are collected in Table 1.

Example 3

150 g of sample E was calcined in air during 3 hours at 923 K, the product is sample F. 120 g of sample F was slurried in 1000 ml of an aqueous 6 molar HCl solution and the slurry was heated during 16 hours at 381 K while stirring. The solids were filtered off and washed three times with 500 ml demineralized water. The filtercake was 16 hours dried in air at 393 K, the dried product is sample G, analytical data are collected in Table 1.

Example 4

100 g of sample G was calcined in air during 3 hours at 923 K, the product is H. 50 g of sample H was slurried in 500 ml of an aqueous 6 molar HCl solution and the slurry was heated during 16 hours at 381 K while stirring. The solids were filtered off and washed three times with 500 ml demineralized water. The filtercake was dried during 24 hours in air at 393 K, the dried product is sample J; analytical data are collected in Table 1.

Example 5

50 g of sample E was slurried in 500 ml of an aqueous 6 molar HCl solution and the slurry was heated during 16 hours at 381 K while stirring. The solids were filtered off and washed three times with 500 ml demineralized water. The filtercake was dried in air during 24 hours at 393 K, the product is sample K; analytical data are collected in Table 1. 25 g of sample K was slurried in 500 ml of an aqueous 6 molar HCl solution and the slurry was heated during 16 hours at 381 K while stirring. The solids were filtered off and washed three times with 500 ml demineralized water. The filtercake was dried during 24 hours in air at 393 K, the dried product is sample L; analytical data are collected in Table 1.

TABLE 1

| Sample | Molar ratio $SiO_2/Al_2O_3$ | $Na_2O$ wt % | Surface area* ($m^2/g$) Total | Outer | Pore Volume (ml/g) Micropores |
|---|---|---|---|---|---|
| 900H | 10 | 0.75 | 460 | 59 | 0.17 |
| PM1-Na | 12.4 | 7.16 | 168 | — | — |
| B | 12.5 | <0.01 | 480 | 61 | 0.20 |
| C | 12.5 | <0.01 | 490 | 60 | 0.20 |
| D | 12.5 | <0.01 | 495 | 85 | 0.19 |
| E | 13.2 | 0.42 | 495 | 72 | 0.20 |
| F | 13.2 | 0.42 | 510 | 76 | 0.20 |
| G | 108 | <0.01 | 486 | 120 | 0.17 |
| H | 108 | <0.01 | 502 | 111 | 0.18 |
| J | 117 | <0.01 | 485 | 113 | 0.18 |
| K | 40 | <0.01 | 509 | 119 | 0.18 |
| L | 44.2 | <0.01 | 499 | 121 | 0.18 |

*measured with Ar using a "Micromeretics ASAP 2000M" and standard procedures.

CATALYST TESTING PROCEDURE

Two procedures were applied for testing the catalysts in the gasphase nitration of benzene in continuous experiments, using a fixed bed reactor, and commercial 65% wt nitric acid. In the first testing procedure (procedure A), which was continued for at least 3 hours the following conditions were applied:

| WHSV benzene | 1 kg.kg.$^{-1}$h$^{-1}$ |
|---|---|
| WHSV nitric acid* | 4 kg.kg.$^{-1}$h$^{-1}$ |
| Temperature | 443K |
| Pressure | atmospheric |

*calculated as 100% wt nitric acid

As carrier gas a 1/1 (v/v) air/$N_2$ mixture was used; the volume ratio carrier gas/benzene(g) was about 1.4.

In the second testing procedure (procedure B), which was continued for at least 20 hours, the following conditions were applied:

| | |
|---|---|
| WHSV benzene | 1 kg.kg.$^{-1}$h$^{-1}$ |
| WHSV nitric acid* | 0.4 kg.kg.$^{-1}$h$^{-1}$ |
| Temperature | 443K |
| Pressure | atmospheric |

*calculated as 100% nitric acid

As carrier gas a 1/1 (v/v) air/N$_2$ mixture or pure nitrogen was used; the volume ratio carrier gas/benzene(g) was about 1.34. In the experiments according to the second testing procedure the partial pressures in mbar of the various components in the gaseous mixture were: Nitric acid: 138; benzene: 281; water: 256; carrier gas: 385.

Before use in the tests the materials were tabletted and subsequently broken in order to obtain a 0.3-0.7 mm sieve fraction. Before being loaded into the reactor the catalysts were either precalcined at 773 K followed by an equilibration in ambient air or they were loaded into the reactor without any pretreatment, other than the catalyst preparation procedure described earlier. Catalysts were in situ pretreated with carrier gas during two hours at reaction temperature, subsequently nitric acid was passed over the catalyst during 0.5 hour, at reaction conditions, as a result of this step an increase in temperature was usually observed. The optimal duration of the pretreatment with nitric acid vapour depends on the reaction conditions and is preferentially sufficiently long to saturate the catalyst with nitric acid under the prevailing conditions. Upon equilibration with nitric acid benzene was introduced in the feed stream, which resulted in a second exothermic effect supposedly due to the excess nitric acid on the catalyst. After a line-out period of one hour the reaction product was collected in a trap cooled to 278 K and filtered with acetone. The composition of the organics in the product was periodically analyzed by a conventional GC method and the non converted nitric acid was determined by titration.

COMPARATIVE EXAMPLES

Test procedure A as described before was applied to measure the catalytic activity in the gasphase nitration of benzene of some generally available materials. In example 6 glasswool was used; in example 7: amorphous silica; in example 8: quartz and in example 9: Norton Zeolon 900H. Results are collected in Table 2.

TABLE 2

| Comparative example 6, 7, 8 and 9 | | |
|---|---|---|
| Example nr | Yield nitrobenzene on benzene fed (%) | Time (hr) |
| 6 | 2 | 2 |
| 7 | 3 | 3 |
| 8 | 12 | 2 |
| 9 | 29 | 2 |

EXAMPLES

Test procedure B as described above was applied to measure the catalytic activity of the following materials: Example 10: Norton Zeolon 900H; example 11: sample B; example 12: sample C; example 13: sample D; example 14: sample E; example 15: sample F; example 16: sample G; example 17: sample H; example 18: sample J; example 19: sample K; example 20: sample L. Results of these experiments are collected in table 3, in all of these experiments the selectivity of the conversion of benzene into nitrobenzene was higher than 99.8%; all experiments were run for at least 20 hours.

TABLE 3

| | Example 10 through 20 | | | | | | | | | | |
|---|---|---|---|---|---|---|---|---|---|---|---|
| | Example nr | | | | | | | | | | |
| | 10 | 11 | 12 | 13 | 14 | 15 | 16 | 17 | 18 | 19 | 20 |
| Nitrobenzene yield on nitric acid in (%)* | 27/10 | 69 | 70 | 70/36 | 64 | 70/63 | 79/76 | 76 | 76 | 67 | 68 |

*in case of catalyst deactivation, the first value represents the number at runhour 3 and the second value refers to runhour 20.

The data in Table 2 show that the glasswool and quartz samples tested here have no catalytic activity in our tests. Amorphous silica and Norton Zeolon 900H show a medium activity and a poor stability. Norton Zeolon 900H, which has according to the manufacturer a SiO$_2$/Al$_2$O$_3$ ratio of 10 is according to EP 53 053, EP 78.247, EP 92.372 and U.S. Pat. No. 4,107,220 the preferred catalyst for the gasphase nitration of aromatics using NO$_2$ as a nitrating agent. In DEOS 28.26.433 and in U.S. Pat. No. 4,418,230, Norton Zeolon 200H, having a SiO$_2$/Al$_2$O$_3$ ratio of 10 is proposed as a catalyst for the gasphase nitration of toluene using nitric acid as nitrating agent. Our results in Table 3 show that the performance of catalysts based on mordenite in the gasphase nitration of benzene is strongly dependent on the method of catalyst preparation and that Norton Zeolon 900H has in comparison with the present mordenite based catalysts generally a low activity and a poor stability.

What is claimed is:

1. A process for the preparation of nitrobenzene, characterized by a gasphase nitration of benzene at a temperature between 400 and 523 K using nitric acid as nitrating agent, in the presence of a H-mordenite zeolite catalyst having a SiO$_2$/Al$_2$O$_3$ molar ration higher than 12 and a Na$_2$O content lower than 0.5 wt %.

2. A process according to claim 1 wherein aqueous nitric acid, having a nitric acid concentration above 50 wt % is used as nitrating agent in the gasphase nitration of benzene.

3. A process according to claim 2 wherein an acidic mordenite zeolite catalyst is applied having a SiO$_2$/Al$_2$O molar ration higher than 40.

4. A process according to claim 2 wherein an acidic mordenite zeolite catalyst is applied having a SiO$_2$Al$_2$O$_3$ molar ration higher than 100.

5. A process according to claim 1, wherein said H-mordenite zeolite catalyst has a Na$_2$O content lower than 0.1 wt %.

* * * * *